United States Patent [19]

Carr et al.

[11] 4,285,958
[45] Aug. 25, 1981

[54] 1-PIPERIDINE-ALKYLENE KETONES, PHARMACEUTICAL COMPOSITIONS THEREOF AND METHOD OF USE THEREOF

[75] Inventors: Albert A. Carr; Joseph E. Dolfini, both of Cincinnati, Ohio; George J. Wright, Richmond, Va.

[73] Assignee: Richardson-Merrell Inc., Wilton, Conn.

[21] Appl. No.: 196,951

[22] Filed: Oct. 14, 1980

Related U.S. Application Data

[62] Division of Ser. No. 28,872, Apr. 10, 1979.

[51] Int. Cl.³ .............. C07D 211/70; A61K 31/445; C07D 211/22
[52] U.S. Cl. ............................ 424/267; 546/237; 546/239; 546/240; 546/241
[58] Field of Search .................. 546/237; 424/267

[56] References Cited

U.S. PATENT DOCUMENTS

| | | | |
|---|---|---|---|
| 3,806,526 | 4/1974 | Carr et al. | 546/208 |
| 3,829,433 | 8/1974 | Carr et al. | 546/213 |
| 3,862,173 | 1/1975 | Carr et al. | 546/212 |
| 3,878,217 | 4/1975 | Carr et al. | 546/213 |
| 3,931,197 | 1/1976 | Carr et al. | 546/237 |
| 3,941,795 | 3/1976 | Carr et al. | 546/213 |
| 3,946,022 | 3/1976 | Carr et al. | 546/208 |
| 3,965,257 | 6/1976 | Carr et al. | 424/248.57 |

Primary Examiner—Robert T. Bond
Attorney, Agent, or Firm—John J. Kolano; Raymond A. McDonald; William J. Stein

[57] ABSTRACT

Pharmaceutically useful compounds of the following formula:

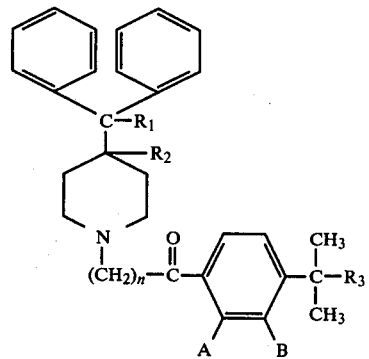

wherein $R_1$ represents hydrogen or hydroxy; $R_2$ represents hydrogen; or $R_1$ and $R_2$ taken together form a second bond between the carbon atoms bearing $R_1$ and $R_2$; n is a positive whole integer of from 1 to 5; $R_3$ is —$CH_3$, —$CH_2OH$, —COOH or —COOalkyl wherein the alkyl moiety has from 1 to 6 carbon atoms and is straight or branched; and A and B are individually hydrogen or hydroxy; with the provisos that at least one of A or B is hydrogen and one of A or B is other than hydrogen when $R_3$ is —$CH_3$; and pharmaceutically acceptable acid addition salts thereof.

12 Claims, No Drawings

1-PIPERIDINE-ALKYLENE KETONES, PHARMACEUTICAL COMPOSITIONS THEREOF AND METHOD OF USE THEREOF

This is a division of application Ser. No. 028,872, filed Apr. 10, 1979.

FIELD OF INVENTION

This invention relates to novel substituted piperidine derivatives. More particularly, this invention relates to substituted phenyl 4-substituted piperidinoalkanone derivatives which are useful as antihistamines, antiallergy agents and bronchodilators and to methods of making and using the same.

BACKGROUND OF INVENTION

Related piperidine derivatives having antihistamine properties are disclosed in the following U.S. patents which are the only material and pertinent references known to applicants:

U.S. Pat. No. 3,806,526 issued Apr. 23, 1974,
U.S. Pat. No. 3,829,433 issued Aug. 13, 1974,
U.S. Pat. No. 3,862,173 issued Jan. 21, 1975,
U.S. Pat. No. 3,878,217 issued Apr. 15, 1975,
U.S. Pat. No. 3,931,197 issued Jan. 6, 1976,
U.S. Pat. No. 3,941,795 issued Mar. 2, 1976,
U.S. Pat. No. 3,946,022 issued Mar. 23, 1976, and
U.S. Pat. No. 3,965,257 issued June 22, 1976.

SUMMARY OF INVENTION

The novel substituted piperidine derivatives of this invention useful as antihistamines, antiallergy agents, and bronchodilators are represented by the formula

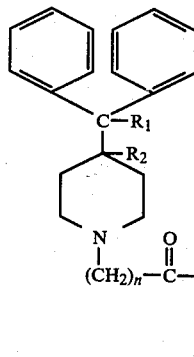

Formula I wherein $R_1$ represents hydrogen or hydroxy; $R_2$ represents hydrogen; or $R_1$ and $R_2$ taken together form a second bond between the carbon atoms bearing $R_1$ and $R_2$; n is a positive whole integer of from 1 to 5; $R_3$ is —$CH_3$, —$CH_2OH$, —COOH or —COOalkyl wherein the alkyl moiety has from 1 to 6 carbon atoms and is straight or branched; and A and B are individually hydrogen or hydroxy; with the provisos that at least one of A or B is hydrogen, and one of A or B is other than hydrogen when $R_3$ is —$CH_3$; and pharmaceutically acceptable acid addition salts thereof.

DETAILED DESCRIPTION OF INVENTION

It can be seen from the above Formula I that compounds of this invention are 4-diphenylmethylpiperidine derivatives as represented by the following Formula II, 4-(hydroxydiphenylmethyl)piperidine derivatives as represented by the following Formula III, or 4-diphenylmethylenepiperidine derivatives as represented by the following Formula IV:

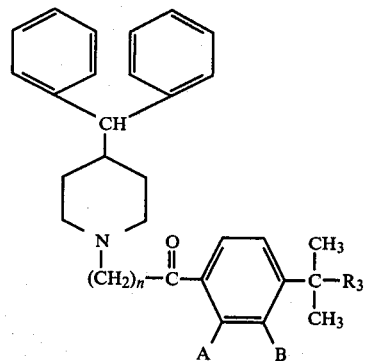

Formula II

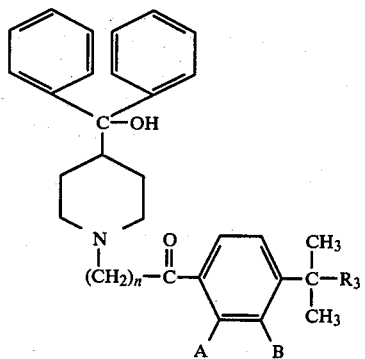

Formula III

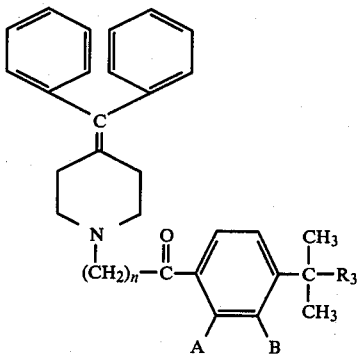

Formula IV

In the above formulas II, III and IV the various symbols n, $R_3$, A and B have the meanings defined in Formula I.

Illustrative examples of straight or branched alkyl groups having from 1 to 6 carbon atoms as referred to herein are methyl, ethyl, n-propyl, isopropyl, n-butyl, sec-butyl, tert-butyl, n-pentyl, neopentyl, n-hexyl.

Preferred compounds of this invention are those of general Formulas III and IV wherein n, $R_3$, A and B have the meanings defined hereinbefore, and may be represented by the following Formula V.

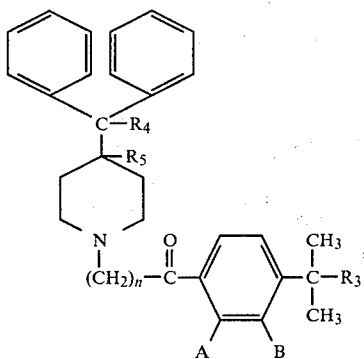

Formula V

In the above Formula V, R₄ represents hydroxy and R₅ represents hydrogen, or R₄ and R₅ taken together form a second bond between the carbon bonds bearing R₄ and R₅; and n, R₃, A and B have the meanings defined in general Formula I.

More preferred compounds of this invention are those of general Formula V wherein n is the integer 3 and B is hydrogen, and of these compounds those wherein R₃ is —COOH are most preferred.

This invention also includes pharmaceutically acceptable salts of the compounds of the hereinbefore set forth formulas. Pharmaceutically acceptable acid addition salts of the compounds of this invention are those of any suitable inorganic or organic acid. Suitable inorganic acids are, for examle, hydrochloric, hydrobromic, sulfuric and phosphoric acids. Suitable organic acids include carboxylic acids, such as, acetic, propionic, glycolic, lactic, pyruvic, malonic, succinic, fumaric, malic, tartaric, citric, cyclamic, ascorbic, maleic, hydroxymaleic, and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, and mandelic acid, sulfonic acids, such as, methanesulfonic, ethanesulfonic and β-hydroxyethanesulfonic acid. Non-toxic salts of the compounds of the above-identified formulas formed with inorganic or organic bases are also included within the scope of this invention and include, for example, those of alkali metals, such as, sodium, potassium and lithium, alkaline earth metals, for example, calcium and magnesium, light metals of group IIIA, for example, aluminum, organic amines, such as, primary, secondary or tertiary amines, for example, cyclohexylamine, ethylamine, pyridine, methylaminoethanol and piperazine. The salts are prepared by conventional means as, for example, by treating the free base of a compound of Formula I with an appropriate acid or when R₃ is COOH a base.

Illustrative examples of compounds of this invention are the following:

4-[4-[4-(hydroxydiphenylmethyl)-1-piperidinyl]-1-oxobutyl]-α,α-dimethylbenzeneacetic acid, 4-[4-[4-(diphenylmethyl)-2-piperidinyl]-1-oxobutyl]-α,α-dimethylbenzeneacetic acid, 4-[4-[4-(diphenylmethylene)-1-piperidinyl]-1-oxobutyl]-α,α-dimethylbenzeneacetic acid, 4-[4-[4-(hydroxydiphenylmethyl)-2-piperidinyl]-1-oxobutyl]-α,α-dimethyl-(3-hydroxybenzene)acetic acid, 4-[4-[4-hydroxydiphenylmethyl)-1-piperidinyl]-1-oxobutyl]-α,α-dimethyl-(2-hydroxybenzene)acetic acid, 4-[4-[4-(diphenylmethylene)-1-piperidinyl]-1-oxobutyl]-α,α-dimethyl-(3-hydroxybenzene)acetic acid, 5-[4-[4-(diphenylmethylene)-1-piperidinyl]-1-oxopentyl]-α,α-dimethylbenzeneacetic acid, 3-[4-[4-(hydroxydiphenylmethyl)-1-piperidinyl]-1-oxopropyl]-α,α-dimethylbenzeneacetic acid, 2-[4-[4-(hydroxydiphenylmethyl)-1-piperidinyl]-1-oxoethyl]-α,α-dimethylbenzeneacetic acid, ethyl 4-[4-[4-(hydroxydiphenylmethyl)-1-piperidinyl]-1-oxobutyl]-α,α-dimethylbenzeneacetate, n-pentyl 4-[4-[4-(diphenylmethyl)-1-piperidinyl]-1-oxobutyl]-α,α-dimethylbenzeneacetate, ethyl 4-[4-[4-(diphenylmethylene)-1-piperidinyl]-1-oxobutyl]-α,α-dimethylbenzeneacetate, methyl 4-[4-[4-(hydroxydiphenylmethyl)-1-piperidinyl]-1-oxobutyl]-α,α-dimethylbenzeneacetate, ethyl 4-[4-[4-(hydroxydiphenylmethyl)-1-piperidinyl]-1-oxobutyl]-α,α-dimethyl-(3-hydroxybenzeneacetate, n-propyl 4-[4-[4-hydroxydiphenylmethyl)-1-piperidinyl]-1-oxobutyl]-α,α-dimethyl-2-hydroxybenzeneacetate, n-hexyl 4-[4-[4-(diphenylmethylene)-1-piperidinyl]-1-oxobutyl]-α,α-dimethyl-3-hydroxybenzeneacetate, ethyl 5-[4-[4-(diphenylmethylene)-1-piperidinyl]-1-oxopentyl]-α,α-dimethylbenzeneacetate, 4'-tert-butyl-2'-hydroxy-4-[4-(hydroxydiphenylmethyl)-1-piperidinyl]butyrophenone, 4'-tert-butyl-3'-hydroxy-4-[4-(hydroxydiphenylmethyl)-1-piperidinyl]butyrophenone, 4'-tert-butyl-2'-hydroxy-4-[4-(diphenylmethylene)-1-piperidinyl]butyrophenone, 4'-tert-butyl-3'-hydroxy-4-[4-(diphenylmethyl)-1-piperidinyl]butyrophenone, 4'-tert-butyl-2'-hydroxy-3-[4-(hydroxydiphenylmethyl)-1-piperidinyl]propionphenone, 4'-tert-butyl-3'-hydroxy-2-[4-(diphenylmethylene)-1-piperidinyl]acetophenone, 4'-(hydroxy-tert-butyl)-2'-hydroxy-4-[4-(hydroxydiphenylmethyl)-1-piperidinyl]butyrophenone, 4'-(hydroxy-tert-butyl)-3'-hydroxy-4-[4-(hydroxdiphenylmethyl)-1-piperidinyl]butyrophenone, 4'-(hydroxy-tert-butyl)-2'-hydroxy-4-[4-(diphenylmethylene)-1-piperidinyl]butyrophenone, 4'-(hydroxy-tert-butyl)-3'-hydroxy-4-[4-(diphenylmethylene)-1-piperidinyl]butyrophenone, 4'-(hydroxy-tert-butyl)-2'-hydroxy-3-[4-(hydroxydiphenylmethyl)-1-piperidinyl]propiophenone, 3'-hydroxy-4'-(hydroxy-tert-butyl)-2-[4-(diphenylmethylene)-1-piperidinyl]acetophenone, 4'-(hydroxy-tert-butyl)-4-[4-(hydroxydiphenylmethyl)-1-piperidinyl]butyrophenone, 4'-(hydroxy-tert-butyl)-4-[4-(diphenylmethylene)-1-piperidinyl]bytrophenone, 4'-(hydroxy-tert-butyl)-3-[4-(diphenylmethyl)-1-piperidinyl]propiophenone, and tert-butyl 2-[4-[4-(hydroxydiphenylmethyl)-1-piperidinyl]-1-oxoethyl]-α,α-dimethylbenzeneacetate.

The compounds of this invention are useful as antihistamines, antiallergy agents and bronchodilators and may be administered alone or with suitable pharmaceutical carriers, and said compounds can be in solid or liquid form such as tablets, capsules, powders, solutions, suspension or emulsions.

The compounds of this invention can be administered orally, parenterally, for example, subcutaneously, intravenously, intramuscularly, intraperitoneally, by intranasal instillation or by application to mucous membranes, such as, that of the nose, throat and bronchial tubes, for example, in an aerosol spray containing small particles of a compound of this invention in a spray or dry powder form.

The quantity of novel compound administered will vary depending on the patient and the mode of administration and can be any effective amount. The quantity of novel compound administered may vary over a wide range to provide in a unit dosage an effective amount of from about 0.01 to 20 mg/kg of body weight of the patient per day to achieve the desired effect. For example, the desired antihistamine, antiallergy and bronchodilator effects can be obtained by consumption of a unit dosage form such as a tablet containing 1 to 50 mg of a novel compound of this invention taken 1 to 4 times daily.

The solid unit dosage forms can be of the conventional type. Thus, the solid form can be a capsule which can be the ordinary gelatin type containing a novel compound of this invention and a carrier, for example, lubricants and inert fillers such as lactose, sucrose or cornstarch. In another embodiment the novel compounds are tableted with conventional tablet bases such as lactose, sucrose or cornstarch in combination with binders such as acacia, cornstarch or gelatin, disintegrating agents such as cornstarch, potato starch or alginic acid, and a lubricant such as stearic acid or magnesium stearate.

The compounds of this invention may also be administered in injectable dosages by solution or suspension of the compounds in a physiologically acceptable diluent with a pharmaceutical carrier which can be a sterile liquid such as water and oils, with or without the addition of a surfactant and other pharmaceutically acceptable adjuvants. Illustrative of oils there can be mentioned those of petroleum, animal, vegetable or synthetic origin, for example, peanut oil, soybean oil or mineral oil, In general, water, saline, aqueous dextrose and related sugar solutions and glycols such as propylene glycol or polyethylene glycol are preferred liquid carriers, particularly for injectable solutions.

For use as aerosols the compounds of this invention in solution or suspension may be packaged in a pressurized aerosol container together with suitable propellants, for example, hydrocarbon propellants, such as, propane, butane or isobutane, or carbon dioxide or nitrogen or other environmentally acceptable propellants with the usual adjuvants as may be necessary or desirable. The compounds also may be administered in a non-pressurized form such as in a nebulizer or atomizer.

The term patient as used herein is taken to mean warm blooded animals, birds, mammals, for examples, humans, cats, dogs, horses, sheep, bovine cows, pigs, lambs, rats, mice and guinea pigs.

To demonstrate the utility of the compounds of this invention ethyl 4-[4-[4-(hydroxydiphenylmethyl)-1-piperidinyl]-1-oxobutyl]-α,α-dimethylbenzeneacetate hydrochloride at a concentration of $1 \times 10^{-7}$ gives a significant reduction in histamine induced isolated guinea pig ileal muscle contraction.

The compounds of this invention are prepared by various means, and certain compounds of the invention are employed to prepare other compounds of the invention as will become apparent by the following.

The compounds of Formula I wherein B is hydrogen $R_3$ is —CH$_3$, —COOH or —COOalkyl wherein the alkyl moiety has from 1 to 6 carbon atoms and is straight or branched and A, n, $R_1$ and $R_2$ have the meanings defined in Formula I are prepared by alkylation of a substituted piperidine derivative of the Formula

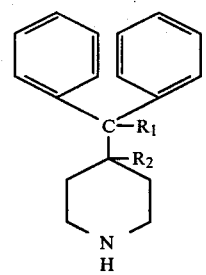

Formula VI with an ω-haloalkyl substituted phenyl ketone of the formula

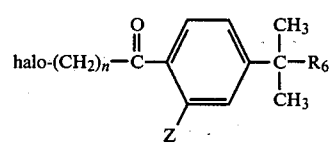

Formula VII wherein halo is a halogen atom, such as, chlorine, bromine or iodine; Z is hydrogen or β-methoxyethoxymethyl-O (memoxy); $R_6$ is —CH$_3$ or —COOalkyl wherein the alkyl moiety has from 1 to 6 carbon atoms and is straight or branched; and $R_1$, $R_2$ and n have the meanings defined in Formula I with the provisos that when either $R_6$ is —CH$_3$ or A in Formula I is hydroxy, Z is memoxy, followed by cleavage of the memory group when A is hydroxy and by base hydrolysis when $R_3$ is Formula I in —COOH. The alkylation reaction is carried out in a suitable solvent, preferably in the presence of a base and optionally in the presence of a catalytic amount of potassium iodide for about 4 to 120 hours and at temperatures of about 70° C. to the reflux temperature of the solvent. Suitable solvents for the alkylation reaction include alcohol solvents, such as, methanol, ethanol, isopropyl alcohol, or n-butanol; ketone solvents, such as, methyl isobutyl ketone; hydrocarbon solvents, such as, benzene, toluene or xylene; halogenated hydrocarbons, such as, chlorobenzene or methylene chloride or dimethylformamide. Suitable bases for the alkylation reaction include inorganic bases, for example, sodium bicarbonate, potassium carbonate, or potassium bicarbonate or organic bases, such as, a trialkylamine, for example, triethylamine or pyridine, or an excess of a compound of Formula VI may be used. Cleavage of the β-methoxyethoxymethyl (MEM) group to give compounds of Formula I wherein A is hydroxy is achieved using trifluoroacetic acid at room temperature or 5 to 8 equivalents of powdered anhydrous zinc bromide in methylene chloride at about 25°–40° C. by the general procedure of E. J. Corey et al., Tetrahedron Letters No. 11, pp. 809–812, 1976. Base hydrolysis of the compounds wherein $R^3$ is —COOalkyl to give the corresponding compounds wherein $R_3$ is —COOH is achieved by treatment with an inorganic base, such as, sodium hydroxide or potassium hydroxide in an aqueous lower alcohol solvent, such as, aqueous methanol, ethanol, isopropyl alcohol or n-butanol at reflux temperature for about ½ hour to 12 hours. When in the compounds of Formula I A is hydroxy and $R_3$ is —COOH, removal of the MEM group prior to base hydrolysis of the ester group is preferred.

The compounds of Formula I wherein $R_3$ is —CH$_3$, —COOH or —COOalkyl, B is hydroxy and A, n, $R_1$ and $R_2$ have the meanings defined in Formula I are prepared by oxidizing the corresponding alcohol derivative of the formula

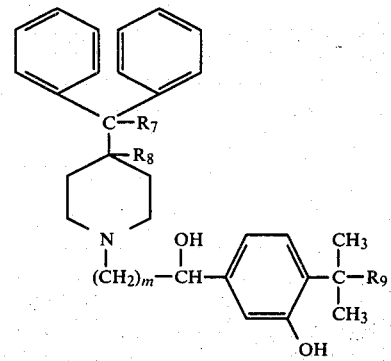

Formula VIII wherein $R_7$ is hydrogen or hydroxy; $R_8$ is hydrogen; or $R_7$ and $R_8$ taken together form a second bond between the carbon atoms bearing $R_7$ and $R_8$; m is an integer of from 1 to 5; and $R_9$ is —CH$_3$; —COOH or —COOalkyl wherein the alkyl moiety is straight or branched and has from 1 to 6 carbon atoms. The oxidation reaction is achieved using various oxidizing reagents. For example, chromium trioxide in pyridine or acetic acid at temperatures of from about 25° C. to 80° C. for about 1 to 8 hours may be employed. Also, aluminum isopropoxide or potassium tert-butoxide in acetone, cyclohexanone or benzophenone usually with an aromatic solvent such as benzene or toluene at about 25° C. to reflux for about 8 to 24 hours may be employed. Another procedure is to use potassium dichromate in dilute sulfuric acid at temperatures of about 0° to 25° C. preferably about 25° C., for about 1 to 8 hours. Also, the oxidation may be achieved using manganese dioxide in methylene chloride at temperatures of about 0° to 40° C. for about 2 to 10 hours.

The compounds of Formula I wherein $R_3$ is —CH$_2$OH are prepared by reducing the corresponding derivative wherein $R_3$ is —COOH or —COOalkyl provided that prior to the reducing reaction the ketone function, that is, the carbonyl group attached to the phenyl ring is protected as a ketal. The ketone moiety is protected as a ketal by treatment with glycols, for example, ethylene glycol, propylene glycol, or 2,2-dimethylpropylene glycol in hydrocarbon solvents, such as, benzene or toluene and in the presence of a catalytic amount of acid, such as, p-toluenesulfonic acid or methanesulfonic acid. During the ketalization step water is removed continuously, for example, in a Dean Stark apparatus, and the reaction is carried out at reflux temperatures for about 4 to 24 hours. Reduction of the ketalized derivative is achieved using, for example, lithium aluminum hydride or diborane in an ether solvent, such as, diethyl ether, tetrahydrofuran or dioxane at reflux temperatures for about 15 minutes to 6 hours. When in the starting material $R_3$ is —COOH the preferred reducing reagent is diborane. When in the starting material $R_3$ is —COOalkyl the preferred reducing reagent is lithium aluminum hydride. Following the reduction reaction the ketone, or carbonyl group, is regenerated by treatment with dilute cold aqueous acid, such as, hydrochloric acid, sulfuric acid or trifluoroacetic acid.

The compounds of Formula VI wherein each of $R_1$ and $R_2$ is hydrogen and wherein $R_1$ is hydroxy and $R_2$ is hydrogen are commercially available. The compounds of Formula VI wherein $R_1$ and $R_2$ form a second bond between the carbon atoms bearing $R_1$ and $R_2$ may be prepared by dehydration of the corresponding compounds wherein $R_1$ is hydroxy by procedures generally known in the art.

The compounds of Formula VII wherein Z is memoxy are prepared by treatment of a phenol of the following Formula IX

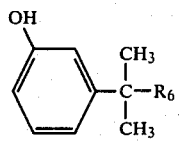

Formula IX with an ω-halo alkanoic acid of the formula halo(CH$_2$)$_n$-COOH wherein $R_6$, halo and n have the meanings defined in Formula VII in the presence of boron trifluoride by the generally described procedure of Delschager and Mousa, Arch. Pharm. 306, 807 (1973). The phenol and acid are melted together at about 50° C. then cooled to about 10° C. after which boron trifluoride is added in an amount about 2.2 times the molar amount of phenol employed. The mixture is heated at about 70° C. for about 2 hours after which the reaction vessel is cooled, vented and treated with a 30% sodium acetate solution and extracted with ether. The organic layer is dried and the residue crystallized to give a hydroxy ketone of the formula

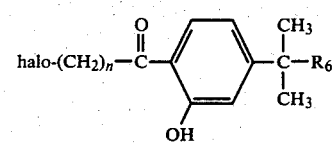

Formula XIII wherein halo is, for example, chlorine or bromine and n is 1 to 5. The hydroxy ketone is then treated with a reagent of the formula CH$_3$OCH$_2$CH$_2$OCH$_2$NEt$_3$+$^{Cl-}$ in acetonitrile according to the general procedure of E. J. Corey et al., Tetrahedron Letters No. 11, pp. 809–812, 1976. The compounds of Formula VII wherein Z is hydrogen are prepared by reacting an appropriate straight or branched lower alkyl C$_{1-6}$ ester of α,α-dimethylphenylacetic acid, which are known in the art or are prepared by procedures well known in the art, with an ω-haloalkanoylC$_{1-6}$-halo compound wherein halo is chlorine, bromine or iodine under the general conditions of a Friedel-Crafts acylation. The reaction is carried out in a solvent such as, carbon disulfide, tetrachloroethane or nitrobenzene with carbon disulfide being a preferred solvent. The reaction time varies from about ½ hour to 8 hours, preferably 3 to 5 hours and the reaction temperature varies from about 0° to 25° C. The ω-haloalkanoylC$_{1\,6}$-halo compounds are commercially available or easily prepared by generally known methods.

The compound of Formula IX wherein $R_6$ is methyl is also commercially available. The compounds of Formula IX wherein $R_6$ is —COOalkyl are prepared by treating a hot solution of 1 equivalent of an appropriate straight or branched alkyl $C_{1-6}$ ester of 3-trifluoroacetoxyphenylacetic acid in dimethoxyethane with a base, such as, sodium hydride under a nitrogen atmosphere followed by the addition of 2.1 equivalents of methyliodide in dimethoxyethane to the mixture over about a 20 minute period. The mixture is refluxed for about 3 hours then concentrated to remove most of the solvent after which diethyl ether, then water are added cautiously. The organic layer is separated, extracted with ether, dried over magnesium sulfate and distilled to give the appropriate ester of $\alpha,\alpha$-dimethyl-3-trifluoroacetoxyphenylacetic acid. To a solution of the methylated ester in 50% alcohol/water is added 3X molar amount of potassium carbonate. The solution is stirred at about 25° C. for about 8 hours then concentrated to a semisolid at reduced pressure at about 50° C., and upon cooling water is added and the mixture is neutralized with dilute hydrochloric acid then extracted with ether. The ether extract is dried over magnesium sulfate, filtered and concentrated to give the appropriate ester of 3-hydroxy-$\alpha,\alpha$-dimethylphenylacetic acid. The esters of 3-trifluoroacetoxyphenylacetic acid are known in the art or may be prepared by procedures generally known in the art, for example, from ethyl m-hydroxyphenylacetate by treatment with trifluoroacetic anhydride.

The compounds of Formula VIII are prepared from a compound of the formula

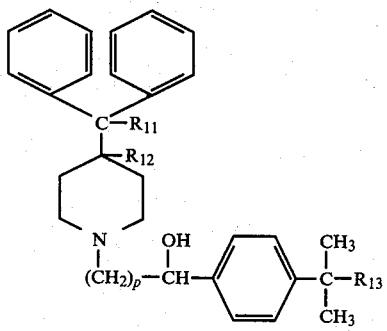

Formula XIV wherein $R_{11}$ is hydrogen or trifluoromethylacetoxy; $R_{12}$ is hydrogen; or $R_{11}$ and $R_{12}$ taken together form a second bond between the carbon atoms bearing $R_{11}$ and $R_{12}$; p is an integer of from 1 to 5; and $R_{13}$ is methyl or —COOalkyl wherein the alkyl moiety has from 1 to 6 carbon atoms and is straight or branched. A compound of Formula XIV is treated with a slight excess of thallium trifluoroacetate intrifluoroacetic acid at reflux temperature (about 72° C.) for about three hours after which one equivalent of lead tetraacetate in trifluoroacetic acid is added. The mixture is stirred for about ½ hour then 1 equivalent of triphenylphosphine is added. Stirring is continued for about ½ hour followed by removal of excess solvent at reduced pressure then the addition of cold and dilute (6 N) hydrochloric acid. The lead chloride and thallium chloride are filtered off, and the filtrate is made alkaline with 10% sodium hydroxide solution and a minimum amount of ethanol is added to bring about complete solution. The solution is refluxed for 4 hours, neutralized, then concentrated, extracted with toluene, dried, filtered and concentrated to give the appropriate compound of Formula VIII wherein $R_9$ is methyl or —COOH. The compounds of Formula VIII wherein $R_9$ is —COOalkyl are obtained by treating 1 equivalent of the corresponding derivative wherein $R_9$ is —COOH with 2 or 3 equivalents of boron trifluoride etherate and about 20 or 30 equivalents of an alcohol of the formula $R_{14}OH$ wherein $R_{14}$ is a straight or branched alkyl group having from 1 to 6 carbon atoms. The mixture is refluxed for about 6 hours, according to the general procedure of Kadaba, J. Pharm. Sci. 63, 1333 (1974). Upon cooling the mixture is added to about 100 ml of water, concentrated at reduced pressure on a water bath, and the product purified by crystallization from lower alcohols or mixtures thereof with toluene.

The compounds of Formula XIV wherein $R_{11}$ is hydrogen or $R_{11}$ and $R_{12}$ together form a second bond between the carbon atoms bearing $R_{11}$ and $R_{12}$ and $R_{13}$ is methyl are known in the art or may be prepared by procedures well known in the art. The compounds of Formula XIV wherein $R_{11}$ is trifluoroacetoxy are prepared by treating a ketone of Formula I wherein $R_1$ is hydroxy and $R_3$ is methyl or —COOalkyl with trifluoroacetic anhydride for about 2 to 6 hours at temperatures of about 0° to 25° C. with stirring followed by catalytic reduction using, for example, platinum oxide in methanol and 1 atmosphere hydrogen in a Paar apparatus to take up an equivalent amount of hydrogen. The compounds of general Formula XIV wherein $R_{11}$ is hydrogen or $R_{11}$ and $R_{12}$ together form a second bond between the carbon atoms bearing $R_{11}$ and $R_{12}$ and $R_{13}$ is —COOalkyl are prepared by reducing the corresponding ketone as represented by Formula I when $R_1$ is hydrogen or $R_1$ and $R_2$ form a second bond using, for example, sodium borohydride or potassium borohydride in a lower alcohol solvent, such as, ethanol or methanol at temperatures ranging from 0° C. to reflux for about ½ hour to 8 hours.

EXAMPLE 1

Ethyl 4-[4-[4-(hydroxydiphenylmethyl)-1-piperidinyl]-1-oxobutyl]-$\alpha,\alpha$-dimethylbenzeneacetate hydrochloride.

(A) To 700 ml of carbon disulfide containing 36.5 g (0.254 mole) of 4-chlorobutyryl chloride is added 74.5 g (0.56 mole) of aluminum chloride with stirring in an ice bath (about —10° C.). Stirring is continued for about 15 minutes at about 25° C. then the mixture is recooled to 5° C. and 48.4 g (0.294 mole) of ethyl $\alpha,\alpha$-dimethylphenylacetate in 100 ml of carbon disulfide is added. The reaction mixture is stirred on an ice bath for 3½ hours then stirred for 15½ hours at 25° C. then poured into HCl-ice water and extracted with chloroform. The extract is washed with dilute sodium carbonate solution, water and saturated sodium chloride solution, dried over magnesium sulfate, and evaporated giving as a solid ethyl 4-(4-chloro-1-oxobutyl)-$\alpha,\alpha$-dimethylphenylacetate.

(B) A mixture of 4.5 g (0.0163 mole) of 4-($\alpha,\alpha$-diphenyl)piperidinemethanol, 6.1 g (0.0205 mole) of ethyl 4-(4-chloro-1-oxobutyl)-$\alpha,\alpha$-dimethylphenylacetate, 5 g (0.05 mole) of potassium bicarbonate and 0.05 g of potassium iodide in 50 ml of toluene is stirred and refluxed for 72 hours then filtered. Ether then ethereal hydrogen chloride is added to the filtrate, and the resulting precipitate collected and recrystallized several times from methanol/butanone and butanone to give ethyl 4-[4-[4-(hydroxydiphenylmethyl)-1-piperidinyl]-1-oxobutyl]-$\alpha,\alpha$-dimethylbenzeneacetate hydrochloride. M.P. 205.5°–208° C.

EXAMPLE 2

4-[4-[4-(Hydroxydiphenylmethyl)-1-piperidinyl]-1-oxobutyl]-α,α-dimethylbenzeneacetic acid A mixture of 1 g of ethyl 4-[4-[4-(hydroxydiphenyl-methyl)-1-piperidinyl]-1-oxobutyl]-α,α-dimethylbenzeneacetate hydrochloride, 25 ml of methanol and 5 ml of 25% sodium hydroxide solution is stirred and refluxed for 2 hours then concentrated to a solid, neutralized with dilute hydrochloric acid and extracted with hot toluene. The toluene extract is filtered and concentrated to a residue which is recrystallized from chloroform/toluene to give 4-[4-[4-(hydroxydiphenylmethyl)-1-piperidinyl[-1-oxobutyl]-α,α-dimethylbenzeneacetic acid.

EXAMPLE 3

4'-(Hydroxy-tert-butyl)-4-[4-(hydroxydiphenylmethyl)-1-piperidinyl]butyrophenone.

A mixture of 1.5 g of the free base of the compound of Example 1, that is, ethyl 4-[4-[4-(hydroxydiphenyl-methyl)-1-piperidinyl]-1-oxobutyl]-α,α-dimethylbenzeneacetate and 25 ml of ethylene glycol containing 0.1 g of p-toluenesulfonic acid is stirred at 100° C. for four hours then concentrated under vacuum to a residue. The residue is triturated with 5% sodium hydroxide solution, extracted with hot toluene, dried over sodium sulfate, filtered and concentrated to give the ketal as a solid. The ketal is added to a 3X excess of lithium aluminum hydride in tetrahydrofuran, stirred and refluxed for 18 hours. The excess lithium aluminum hydride is decomposed with water and the reaction mixture is concentrated to a solid residue. The residue is extracted with hot toluene, stirred over 10% aqueous HCl for 1 hour then made basic and extracted with chloroform, dried over magnesium sulfate, filtered and concentrated to give 4'-(hydroxy-tert-butyl)-4-[4-(hydroxydiphenyl-methyl)-1-piperidinyl]butyrophenone.

EXAMPLE 4

4'-tert-Butyl-2'-hydroxy-4-[4-(hydroxydiphenylmethyl)-1-piperidinyl]butyrophenone (A) A solution of 0.10 mole of 3-tert-butylphenol in 0.20 mole of ω-chlorobutyric acid is heated in a pressure vessel at 50° C. for about 1 hour then cooled to 10° C. after which 0.35 mole of boron trifluoride is added. The vessel is sealed and the mixture is heated to about 70° C. for about 2 hours after which the mixture is cooled, the vessel vented and 200 ml of a 30% solution of sodium acetate is added followed by extraction with ether to give 4'-tert-butyl-2'-hydroxy-4-chlorobutyrophenone. The phenone is treated with a 10% excess of β-methoxyethoxymethyl triethylammonium chloride (CH$_3$OCH$_2$CH$_2$OCH$_2$N(C$_2$H$_5$)$_3$+ Cl−) in 250 ml of dry acetonitrile with stirring for 18 hours at about 25° C. The precipitated triethylamine hydrochloride is filtered, and the filtrate concentrated to a semi-solid which is dissolved in dry ether. Residual amounts of triethylamine are removed by filtration. Concentration of the ether solution gives 4'-tert-butyl-2'-memoxy-4-chlorobutyrophenone.

(B) When in the procedure of Example 1 (B) an appropriate amount of 4'-tert-butyl-4-chloro-2'-memoxybutyrophenone is substituted for ethyl 4-(4-chloro-1-oxobutyl)-α,α-dimethylphenylacetate, 4'-tert-butyl-2'-memoxy-4-[4-(hydroxydiphenylmethyl)-1-piperidinyl]-butyrophenone is obtained and treated with excess trifluoroacetic acid at room temperatures for 0.2–1.0 hours followed by removal of the trifluoroacetic acid at reduced pressure and then neutralized with dilute sodium bicarbonate solution. The organic layer is separated, dried (magnesium sulfate) and concentrated to give 4'-tert-butyl-2'-hydroxy-4-[4-(hydroxydiphenyl-methyl)-1-piperidinyl]butyrophenone.

EXAMPLE 5

When in the procedure of Example 1(B) an appropriate amount of 4-(diphenylmethylene)piperidine or 4-(diphenylmethyl)piperidine is substituted for 4-(α,α-diphenyl) piperidinemethanol the following respective products are obtained: ethyl 4-[4-[4-(diphenylmethylene)-1-piperidinyl]-1-oxobutyl]-α,α-dimethylbenzeneacetate hydrochloride, and ethyl 4-[4-[4-(diphenylmethyl)-1-piperidinyl]-1-oxobutyl]-α,α-dimethylbenzeneacetate hydrochloride.

EXAMPLE 6

When in the procedure of Example 2 an appropriate amount of ethyl 4-[4-[4-(diphenylmethylene)-1-piperidinyl]-1-oxobutyl]-α,α-dimethylbenzeneacetate hydrochloride or ethyl 4-[4-[4-(diphenylmethyl)-1-piperidinyl]-1-oxobutyl]-α,α-dimethylbenzeneacetate hydrochloride is substituted for ethyl 4-[4-[4-(hydroxydiphenylmethyl)-1-piperidinyl]-1-oxobutyl]-α,α-dimethylbenzeneacetate hydrochloride the following respective products are obtained: 4-[4-[4-(diphenylmethylene)-1-piperidinyl]-1-oxobutyl]-α,α-dimethylbenzeneacetic acid and 4-[4-[4-(diphenylmethyl)-1-piperidinyl]-1-oxobutyl]-α,α-dimethylbenzeneacetic acid.

It is readily apparent to one skilled in the art that upon substitution of an appropriate amount of the free base of the products of Example 5 for the starting material free base of Example 3 the following respective products are obtained: 4'-(hydroxy-tert-butyl)-4-[4-(diphenylmethylene)-1-piperidinyl]butyrophenone, and 4'-(hydroxy-tert-butyl)-4-[4-(diphenylmethyl)-1-piperidinyl]butyrophenone.

EXAMPLE 7

Ethyl 4-[4-[4-(hydroxydiphenylmethyl)-1-piperidinyl]-1-oxobutyl]-α,α-dimethyl-3-hydroxyphenylacetate (A) A hot solution of 1 equivalent of ethyl 3-trifluoroacetoxyphenylacetate in dimethoxyethane is treated with 2.1 equivalents in sodium hydride under a nitrogen atmosphere followed by the addition of 2.1 equivalents of methyliodide in dimethoxyethane over about a 20 minute period. The mixture is refluxed for about 3 hours then concentrated to remove most of the solvent after which diethyl ether, then water are added cautiously. The organic layer is separated, extracted with ether, dried over magnesium sulfate, and distilled to give ethyl α,α-dimethyl-3-trifluoroacetoxyphenylacetate. To a solution of the methylated ester in 50% alcohol/water is added 3X molar amount of potassium carbonate. The solution is stirred at 25° C. for 8 hours then concentrated to a semisolid at reduced pressure at 50° C. Upon cooling water is added and the mixture is neutralized with dilute hydrochloric acid then extracted with ether. The ether extract is dried over magnesium sulfate, filtered and concentrated to give ethyl α,α-dimethyl-3-hydroxyphenylacetate.

When in the procedure of Example 4(A) an appropriate amount of ethyl α,α-dimethyl-3-hydroxyphenylacetate is substituted for 3-tert-butylphenol, ethyl 4-(4-chlorobutyryl)-3-memoxy-α,α-dimethylphenylacetate is obtained.

(B) When in the procedure of Example 1(B) an appropriate amount of ethyl 4-(4-chlorobutyryl)-3-memoxy-α,α-dimethylphenylacetate is substituted for ethyl 4-(4-chloro-1-oxobutyl)-α,α-dimethylphenylacetate, ethyl 4-[4-(hydroxydiphenylmethyl)-1-piperidinyl]-1-oxobutyl]-α,α-dimethyl-3-memoxyphenylacetate is obtained. One equivalent of the memoxy acetate is treated with excess trifluoroacetic acid at room temperature for 0.5 hour. The resulting solution is concentrated to a solid at room temperature and reduced pressure. The residue is triturated with ethyl acetate and shaken over dilute sodium bicarbonate solution. The organic layer is separated, dried and concentrated to give ethyl 4-[4-[4-(hydroxydiphenylmethyl)-1-piperidinyl]-1-oxobutyl]-α,α-dimethyl-3-hydroxyphenylacetate.

The above obtained acetate derivative is converted to 4-[4-[4-(hydroxydiphenylmethyl)-1-piperidinyl]-1-oxobutyl]-α,α-dimethyl-3-hydroxyphenylacetic acid by refluxing with 25% aqueous sodium hydroxide in methanol according to the procedure of Example 2 above.

EXAMPLE 8

4'-tert-Butyl-3'-hydroxy-4-[4-(hydroxydiphenylmethyl)-1-piperidinyl]butyrophenone (A) A mixture of 0.1 mole of 4'-tert-butyl-4-[4-(hydroxydiphenylmethyl)piperidinyl]butyrophenone in 30 ml of trifluoroacetic anhydride is stirred for 4 hours at 0° C., concentrated to a solid, then reduced catalytically in a Paar apparatus using platinum oxide in 200 ml of ethyl acetate until an equivalent amount of hydrogen is taken up to give α-(p-tert-butylphenyl)-4-(α-trifluoromethylacetoxy-α-phenylbenzyl)-1-piperidinebutanol which after removal of catalyst and solvent is treated with a slight excess of thallium trifluoroacetate in 50 ml of trifluoroacetic acid at 72° C. for 3 hours after which 1 equivalent of lead tetraacetate in 10 ml of trifluoroacetic acid is added. The mixture is stirred for 30 minutes then 1 equivalent of triphenylphosphine is added. Stirring is continued for 30 minutes then the excess solvent is removed at reduced presure. Cold and dilute (6 N) hydrochloric acid (100 ml) is added and the mixture is filtered. The filtrate is made basic using 10% aqueous sodium hydroxide and a minimum amount of ethanol is added to bring about complete solution. The solution is refluxed 4 hours, neutralized with dilute HCl, concentrated, extracted with toluene dried, filtered and concentrated to give α,α-diphenyl-1-(4-(4-tert-butyl-3-hydroxy)phenyl-4-hydroxy)butyl-4-piperidinemethanol.

To 0.25 mole of potassium tert-butoxide is added 500 ml of toluene, 0.1 mole of α,α-diphenyl-1-(4-(4-tert-butyl-3-hydroxy)phenyl-4-hydroxy)butyl-4-piperidinemethanol and 0.5 mole of benzophenone. The mixture is flushed with dry nitrogen and refluxed for 10 hours. The reaction mixture is then cooled and neutralized using dilute hydrochloric acid. The organic phase is separated, dried over magnesium sulfate, filtered and treated with ethereal HCl. The resulting precipitate is collected and purified by recrystallization from methanolbutanone to give 4'-tert-butyl-3'-hydroxy-4-[4-(hydroxydiphenylmethyl)-1-piperidinyl]butyrophenone hydrochloride.

EXAMPLE 9

An illustrative composition for hard gelatin capsules is as follows:

| | |
|---|---|
| (a) Ethyl 4-[4-[4-(hydroxydiphenylmethyl)-1-piperidinyl]1-oxobutyl]-α,α-dimethylbenzeneacetate hydrochloride | 10 mg |
| (b) talc | 5 mg |
| (c) lactose | 100 mg |

The formulation is prepared by passing the dry powders of (a) and (b) through a fine mesh screen and mixing them well. The powder is then filled into hard gelatin capsules at a net fill of 115 mg per capsules.

EXAMPLE 10

An illustrative composition for tablets is as follows:

| | |
|---|---|
| (a) Ethyl 4-[4-[4-(hydroxydiphenylmethyl)-1-piperdinyl]-1-oxobutyl]-α,α-dimethylbenzeneacetate hydrochloride | 5 mg |
| (b) starch | 43 mg |
| (c) lactose | 60 mg |
| (d) magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 11

An illustrative composition for an aerosol solution is the following:

| | Weight percent |
|---|---|
| (a) 4'-(Hydroxy-tert-butyl)-4-[4-(hydroxydiphenylmethyl)-1-piperidinyl]butyrophenone | 5.0 |
| (b) ethanol | 35.0 |
| (c) isobutane | 60.0 |

The materials (a), (b) and (c) are packaged in 15 ml stainless steel containers equipped with a metering valve designed to meter 0.2 grams per dose, an equivalent of 10 mg of novel compound (a).

EXAMPLE 12

An illustrative composition for an aerosol suspension is the following:

| | Weight percent |
|---|---|
| (a) 4-[4-[4-(Hydroxydiphenylmethyl)-1-piperidinyl]-1-oxobutyl]-α,α-dimethylbenzeneacetic acid (Particle size <10μ) | 20.0 |
| (b) sorbitan trioleate | 0.5 |
| (c) propane | 79.5 |

The materials (a)–(c) are packaged in 15 ml stainless steel containers equipped with a metering valve designed to meter 50 mg per dose, an equivalent of 10 mg of novel compound (a).

EXAMPLE 13

An illustrative composition for an injectable suspension is the following 1 ml ampul for an intramuscular injection.

|   | Weight percent |
|---|---|
| (a) Ethyl 4-[4-[4-(hydroxydiphenyl-methyl)1-piperidinyl]-1-oxobutyl]-α,α-dimethylbenzeneacetate hydrochloride (particle size <10μ) | 1.0 |
| (b) polyvinylpyrrolidone (M.W. 25000) | 0.5 |
| (c) lecithin | 0.25 |
| (d) water for injection to make | 100.0 |

The materials (a)–(d) are mixed, homogenized, and filled into 1 ml ampuls which are sealed and autoclaved 20 minutes at 121° C. Each ampul contains 10 mg per ml of novel compound (a).

We claim:

1. A compound of the formula

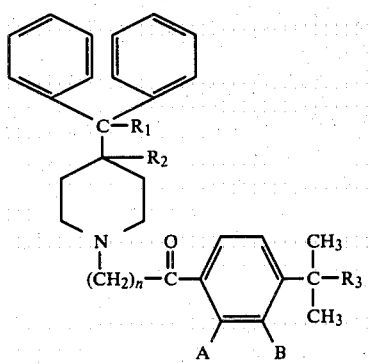

wherein $R_1$ is hydrogen or hydroxy; $R_2$ is hydrogen; or $R_1$ and $R_2$ taken together form a second bond between the carbon atoms bearing $R_1$ and $R_2$; n is an integer of from 1 to 5; $R_3$ is —$CH_3$, or —$CH_2OH$; and A and B are individually hydrogen or hydroxy; with the provisos that at least one of A or B is hydrogen, and one of A or B is other than hydrogen when $R_3$ is —$CH_3$; and pharmaceutically acceptable acid addition salts thereof.

2. A compound of claim 1 wherein $R_1$ is hydroxy or $R_1$ and $R_2$ taken together form a second bond between the carbon atoms bearing $R_1$ and $R_2$.

3. A compound of claim 2 wherein $R_3$ is —$CH_3$.

4. A compound of claim 2 wherein $R_3$ is —$CH_2OH$.

5. A compound of claim 2 wherein $R_1$ is hydroxy.

6. A compound of claim 1 wherein $R_1$ is hydroxy, n is 3 and B is hydrogen.

7. A compound of claim 1 wherein $R_1$ and $R_2$ together form a second bond between the carbon atoms bearing $R_1$ and $R_2$, n is 3 and B is hydrogen.

8. A compound of claim 1 which is 4'-tert-butyl-2'-hydroxy-4-[4-(hydroxydiphenylmethyl)-1-piperidinyl]-butyrophenone or a pharmaceutically acceptable salt thereof.

9. A compound of claim 1 which is 4'-(hydroxy-tert-butyl)-4-[4-(hydroxydiphenylmethyl)-1-piperidinyl]-butyrophenone or a pharmaceutically acceptable salt thereof.

10. A compound of claim 1 which is 4'-(hydroxy-tert-butyl)-4-[4-(diphenylmethylene)-1-piperidinyl]-butyrophenone or a pharmaceutically acceptable salt thereof.

11. A pharmaceutical composition in unit dosage form which comprises an effective antiallergic amount of a compound of claim 1 or a pharmaceutically acceptable salt thereof and a significant amount of a pharmaceutically acceptable carrier.

12. A method of treating allergic reactions in a patient in need thereof which comprises administering to said patient an anti-allergically effective amount of a compound of claim 1.

* * * * *